United States Patent [19]

Jiu et al.

[11] 3,994,933

[45] Nov. 30, 1976

[54] 3-OXO-PREGNA-4,17(20)-DIEN-20-CARBOXYLIC ACID AND ESTERS

[75] Inventors: James Jiu, Morton Grove, Ill.; William J. Marsheck, Harbor Beach, Mich.

[73] Assignee: G. D. Searle & Co., Chicago, Ill.

[22] Filed: Apr. 30, 1975

[21] Appl. No.: 573,030

[52] U.S. Cl. .............................. 260/397.1; 195/51 R
[51] Int. Cl.$^2$ .............................................. C07J 9/00
[58] Field of Search ................................. 260/397.1

[56] References Cited
UNITED STATES PATENTS 3,816,480  6/1974  Lenz ................................ 260/397.1

FOREIGN PATENTS OR APPLICATIONS 749,198  5/1956  United Kingdom .............. 260/397.1

*Primary Examiner*—Elbert L. Roberts
*Attorney, Agent, or Firm*—John J. McDonnell

[57] ABSTRACT

The present invention is concerned with the preparation of 3-oxo-pregna-4,17(20)-dien-21-carboxylic acid and esters thereof by the microbial degradation of fucosterol, cholesterol, stigmasterol, campesterol or sitosterol with Mycobacterium sp. NRRL B-8054. The compounds of the present invention are useful antispasmodic agents and are also active against influenza virus.

3 Claims, No Drawings

3-OXO-PREGNA-4,17(20)-DIEN-20-CARBOXYLIC ACID AND ESTERS

The present invention is concerned with the preparation of 3-oxo-pregna-4,17(20)-dien-20-carboxylic acid, lower alkyl esters thereof, and pharmaceutically acceptable acid salts.

Fucosterol, cholesterol, stigmasterol, campesterol, sitosterol or mixtures thereof are fermented with Mycobacterium sp. NRRL B-8054* to provide 3-oxo-pregna-4,17(20)-dien-21-carboxylic acid and methyl-3-oxo-pregna-4,17(20)-dien-20-carboxylate. The 3-oxo-pregna-4,17(20)-dien-21-carboxylic acid may be converted to the corresponding lower alkyl ester by acid catalysed esterification in an aqueous solution of a lower alkanol. Pharmaceutically acceptable acid salts are prepared by reaction of the acid with an appropriate base. Pharmaceutically acceptable acid salts include sodium, potassium, calcium, ammonium and the like. Thus the present invention encompasses compounds of the formula

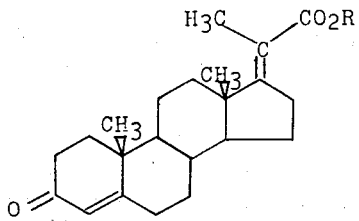

wherein R is hydrogen, loweralkyl having 1–7 carbon atoms or a pharmaceutically acceptable cation.

* NRRL culture are deposited at ARS Culture Collection, 1815 North University Street, Peoria, Illinois 61604, under conditions such that they are permanently available to the public.

The present invention also encompasses a process for preparing a compound of the formula above wherein R is hydrogen or methyl comprising fermenting fucosterol, cholesterol, stigmasterol, sitosterol, campesterol or mixtures thereof with *Mycobacterium* sp. NRRL B-8054 in a suitable growth medium and isolating said compounds. A mixture of sitosterol and campesterol is the preferred substraight.

The compounds to which this invention relates are useful by reason by their valuable biological properties. In particular, they are anti-spasmodic.

The anti-spasmodic utility of the instant compounds is evident from the results of a standardized test for their capacity to antagonize the activity of bradykinin, prostaglandin $E_2$ ($PGE_2$) and/or acetylcholine. The procedure, carried out substantially as described by J. H Sanner in Arch. intern. Pharmacodynamie, 180, 46 (1969), is as follows:

A female guinea pig weighing between 200 and 500 g is sacrificed by cervical dislocation, whereupon the ileum is quickly removed and a 2-cm segment thereof mounted in a 5-ml tissue bath containing modified Tyrode solution and adapted to record isotonic contractions. The Tyrode solution, at 37° C and constantly bubbled with a mixture of 95% oxygen and 5% carbon dioxide (V/V), consists of 8.046 g of NaCl, 0.200 g of KCl, 0.132 g of $CaCl_2.2H_2O$, 0.107 g of $MgCl_2.6H_2O$, 1.000 g of $NaHCO_3$, 0.058 g of $NaH_2PO_4.H_2O$, 1.000 g of dextrose, and $H_2O$ q.s. 1 l. Doses of bradykinin, $PGE_2$, and acetylcholine necessary to induce approximately equal submaximal contractions are experimentally determined, whereupon two sets of three (one for each agonist at the predetermined dose) such contractions are recorded at 4-minute intervals as controls. The modified Tyrode solution is immediately replaced by a solution of suspension of test compound therein, at 37° C and bubbled as before, following which three sets of contractions induced by the three agonists at the predetermined doses are recorded, beginning 4 minutes after the second control recording and continuing at 4-minute intervals thereafter. The first of these three sets serves only to maintain the dosage timing until the tissue is in equilibrium with the test compound. The last two sets are compared with the two control sets, and a compound is considered active vis-a-vis a given agonist if the mean contraction induced thereby in the presence of compound is not more than 25% of the mean control contraction for that agonist. The initial screening dose in this test is ordinarily 30 mcg per ml.

The compounds of the present invention are also useful by virtue of their activity against influenza virus. This activity is witnessed by the following test:

Cell cultures of primary Rhesus monkey kidney maintained in 25 cc. plastic flasks and each containing test compound at concentrations of 625, 125, 25, 5, or 1 microgram per milliliter are prepared in pairs. These flasks, and an identical pair of flasks containing no test compound, are each innoculated with a dose of influenza virus type A (strain 575) previously shown to produce maximum hemadsorption and minimum cytopathogenic effects after a 24 hour incubation. Where the cultures contain test compound, the virus is added 1 hour after addition of the compound to the culture. After 24 hours incubation of the cultures, the supernatant fluids are removed and 3.0 ml. of a 0.4% suspension of guinea pig erythrocytes are added to each flask. The flasks are then incubated at 4° C in a horizontal position for 30 minutes. The flasks are rocked every 10 minutes during the incubation period. After this incubation, the red cell suspension is decanted from each flask, the flasks are washed twice with 3.0 ml. of phosphate buffer solution (pH 7.4) to remove unadsorbed red cells, and 3.0 ml. of distilled water is then added to lyse the adsorbed cells. The flasks are then further incubated at 37° C for 30 minutes in a horizontal position and the flasks are rocked every 10 minutes. After this incubation, the fluid contents of the pairs of flasks are combined to form an assay unit and are placed at room temperature for 15–30 minutes to allow settling of cellular debris. A pair of control flasks identical with the above, except for the absence of test compound and virus inoculation, is run concurrently. The resulting hemoglobin solutions from each assay unit are then read for optical density in a Beckman spectrophotometer at about 415 millimicrons. A test compound is considered active if, at one of the tested levels, it reduces the optical density reading by at least 50% relative to the virus control.

Those skilled in the art will recognize that observations of activity in standardized tests for particular biological effects are fundamental to the development of valuable new drugs, both veterinary and human.

Fermentation is ordinarily carried out in the medium wherein the organism is cultured. However, it is likewise possible to separate the bacterial cells from the culture medium by centrifugation or other means and use the resultant cellular matter to implement the fermentation. Moreover, the cells can be ruptured ultrasonically or otherwise to facilitate access to enzymes present, which can be isolated by filtration or extracted with a solvent such as acetone or water and substituted for the organism or cells thereof.

A nutrient medium is required for culture of the organism, which is to say one containing assimilable nitrogen and carbon; and an adequate supply of sterile air should be maintained therein, for example by exposing a large surface of the medium to the air or preferably passing it through the medium in quantities sufficient to support submerged growth.

Suitable nitrogen sources are those normally employed for the purpose, including soy bean meal, corn steep liquor, meat extract, protein (optionally digested) peptone, yeast extract, distillers' solubles, casein hydrolysate, malate, and/or ammonium compounds. All of the foregoing materials excepting sometimes the last two serve also as carbon sources. Other carbon-containing substances satisfactory and conventionally used as nutrients are the carbohydrates, for example glycerol, glucose, fructose, sucrose, lactose, maltose, inositol, dextrin, starch, and whey, among which inositol is additionally useful because of its unusual capacity to stimulate growth.

Phosphate, magnesium, and/or ferrous ions likewise may be incorporated in the culture medium as growth-promoting factors if desired; butters may be added to assure that growth is initiated at a substantially neutral pH; and wetting agents may be employed to improve contact between the steroid and the fermenting agent. An antifoaming agent is usually beneficial. Where isolated cells or enzymes are used to induce fermentation rather than the intact and growing organism, nutrients need not, of course, be present; but in either event the medium is customarily preponderantly aqueous.

Concentration of the steroid substrate in the medium, as also fermentation time and temperature, can vary widely; and such operating conditions are to a certain extent interdependent. A preferred but a critical range of concentrations of the substrate is 0.01–1.0%, while fermentations of from 2 hours to 10 days duration at temperatures between 24° and 35° C are representative. Manifestly, conditions must not be so stringent as to destroy the substrate, kill the organism prematurely, or inactivate the involved enzymes.

In a preferred embodiment of the invention, a nutrient medium containing 0.1% of substrate is sterilized by heating at around 120° C for 1 hour and then aerobically incubated at 30°–32° C with a culture of *Mycobacterium* sp. NRRL B 8054 for approximately 1 week. Alternatively, the substrate is introduced just prior to inoculation, or during the second or third day of incubation when the culture has developed. Products are extracted with dichloromethane and isolated by chromatography.

The following examples are directed to illustrating, variously and in detail, this invention. However, the invention is not to be construed as limited thereby, either in spirit or in scope, since it will be apparent to those skilled in the art that many modifications, both of materials and of techniques, may be practiced without departing from the purpose and intent of this disclosure.

In the examples hereinafter set forth, temperatures are given in degrees Celsius and relative amounts of materials in parts by weight, except as otherwise noted. Distribution of the substrate throughout the medium is facilitated by introducing it in the form of a suspension prepared by ultrasonically dispersing each 5 parts thereof in 200 parts of water containing 0.1 part of polyoxyethylene sorbitan monooleate (Tween 80). Foaming is controlled by adding 0.1 percent of a dimethypolysiloxane emulsion (Dow Corning Antifoan EG 10) to the medium prior to sterilization.

Yields are calculated according to the formula $$Y = \frac{100P}{Q(S-R)}$$

where Y represents percent yield, P weight of product, Q molecular weight of product divided by molecular weight of substrate, S initial weight of substrate, and R weight of recovered substrate. Conversions are calculated according to the formula $$C = \frac{100P}{QS}$$

wherein C represents percent conversion and P, Q, and S retain the meanings previously assigned.

The compounds of the present invention are useful hypolipoproteinemia agents as determined by methods set out by Portes et al. Arch. Biochemm. Biophys. 151, 128–136 (1972) and Goodwin and Margolis, J. Biol. Chem. 248, 7610–7613 (1973).

EXAMPLE 1

To a medium consisting of 25 parts of peptone, 15 parts of meat extract, 5 parts of yeast extract, and 4000 parts of tap water is added 5 parts of sitosterolscampesterol mixture (55/45). The resultant mixture is sterilized by heating 1 hour at 121° C, whereupon it is cooled to 30° ± 1° C and then inoculated with 500 parts of fluid culture of *Mycobacterium* sp. NRRL B-8054. The inoculated mixture is incubated at 30 ± 1° C for 168 hours while sterile air is passed through and the developing culture is agitated to induce submerged growth. Following incubation, the mixture is extracted with dichloromethane. The extract is dried over anhydrous sodium sulfate and filtered through diatomaceous earth. The filtrate is stripped of solvent by vacuum distillation and the residue is taken up in ethyl acetate and chromatographed on silica gel, using ethyl acetate and Skelly Solve B as eluent.

From eluates comprising 15% ethyl acetate in Skelly Solve B, on evaporation of solvent provides a crude product which is recrystallized from methanol to provide methyl 3-oxo-pregna-4,17(20)-dien-20-carboxylate, melting at 149°–151° C. This compound has the following structural formula

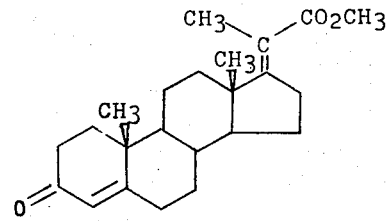

Fractions eluted with 20–50 ethyl acetate are pooled and dissolved in 10% ethyl acetate in methylene chloride and recrystallization from methanol provides 3- oxo-pregna-4,17(20)-dien-20-carboxylic acid melting at 266°–270° C. This compound has the following structural formula

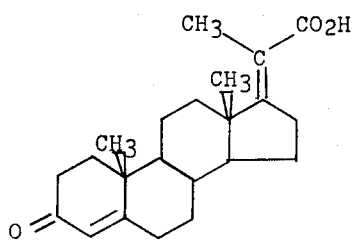

Acid catalyzed esterification of this acid with ethanol provides the corresponding ethyl ester; ethyl 3-oxo-pregna-4,17(20)-dien-20-carboxylate.

EXAMPLE 2

Following the procedure set out in Example 1 using equivalent parts of a sitosterol-campesterol mixture (63/37) likewise produces the compounds shown in Example 1.

EXAMPLE 3

Following the procedure set out in Example 1 using equivalent parts of a sitosterol-campesterol mixture (91/9) likewise produces the compounds shown in Example 1.

EXAMPLE 4

Following the procedure set out in Example 1 using equivalent parts of fucosterol provides the compounds shown in Example 1.

EXAMPLE 5

Following the procedure set out in Example 1 using equivalent parts of cholesterol provides the compounds shown in Example 1.

EXAMPLE 6

Following the procedure set out in Example 1 using equivalent parts of stigmasterol provides the compounds shown in Example 1.

What is claimed is:
1. A compound of the formula

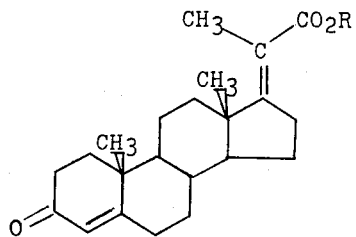

wherein R is hydrogen, loweralkyl having 1–7 carbon atoms or a pharmaceutically acceptable cation.
2. A compound according to claim 1 which is 3-oxo-pregna-4,17(20)-dien-20-carboxylic acid.
3. A compound according to claim 1 which is methyl-3-oxo-pregna-4,17(20)-dien-20-carboxylate.

* * * * *